United States Patent
Schonfeld

[11] Patent Number: 6,018,835
[45] Date of Patent: Feb. 1, 2000

[54] APPARATUS FOR CLEANING A STETHOSCOPE

[76] Inventor: Alvin J. Schonfeld, P.O. Box 6998, Avon, Colo. 81620-6998

[21] Appl. No.: 09/013,443

[22] Filed: Jan. 26, 1998

[51] Int. Cl.⁷ .................................................. A47L 1/02
[52] U.S. Cl. ......................... 15/97.1; 422/300; 134/57 R; 134/198
[58] Field of Search ................................ 15/97.1, 103.5, 15/99, 97.2, 101, 22.3, 21.1; 422/292, 300; 134/57 R, 198

[56] References Cited

U.S. PATENT DOCUMENTS

| | | | |
|---|---|---|---|
| 2,082,991 | 6/1937 | Turco | 422/300 |
| 2,463,208 | 3/1949 | Schutten | 422/300 |
| 2,952,859 | 9/1960 | Alcamo | 15/97.1 |
| 3,126,247 | 3/1964 | Miller | 15/21.1 |
| 4,073,376 | 2/1978 | Krooss | 15/97.1 |
| 4,280,244 | 7/1981 | Spirig | 15/97.1 |
| 4,288,882 | 9/1981 | Takeuchi . | |
| 4,354,292 | 10/1982 | Telestad et al. | 15/103.5 |
| 4,918,778 | 4/1990 | Chupin et al. | 15/97.1 |
| 5,074,322 | 12/1991 | Jaw | 422/300 |
| 5,132,518 | 7/1992 | Solacoff . | |
| 5,466,898 | 11/1995 | Gilbert . | |
| 5,486,659 | 1/1996 | Rosenbush . | |
| 5,641,464 | 6/1997 | Briggs, III et al. | 422/300 |
| 5,769,099 | 6/1998 | Davis et al. | 15/97.1 |

Primary Examiner—Robert J. Warden, Sr.
Assistant Examiner—Kaj K. Olsen
Attorney, Agent, or Firm—John W. Harbst

[57] ABSTRACT

An apparatus for cleaning a head portion of a medical stethoscope. The head portion of the stethoscope includes a diaphragm capable of transducing medical sounds when positioned during use in juxtaposition relative to a patient. The cleaning apparatus of the present invention includes a housing defining an interior cleaning chamber and having an opening communicating between an exterior of the housing and the cleaning chamber. The opening in the housing permits the head portion of the stethoscope to be inserted into the cleaning chamber. An apparatus is arranged in the cleaning chamber for disinfecting the head portion of the stethoscope inserted through the opening.

26 Claims, 7 Drawing Sheets

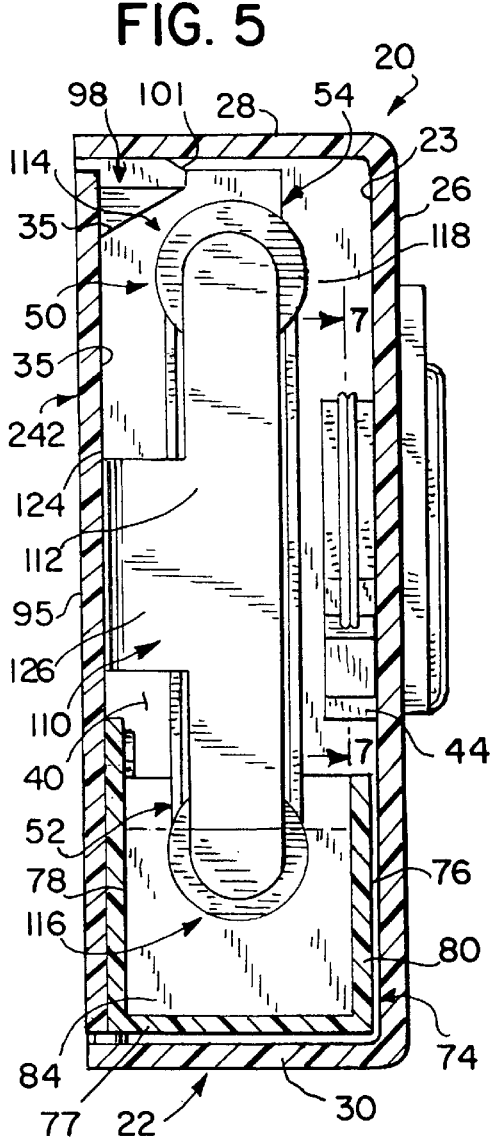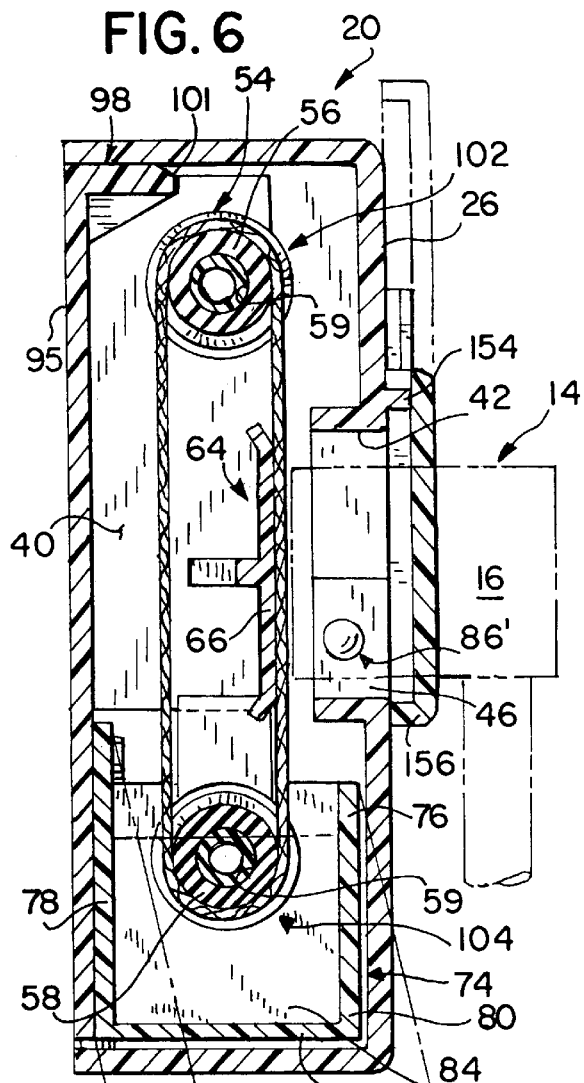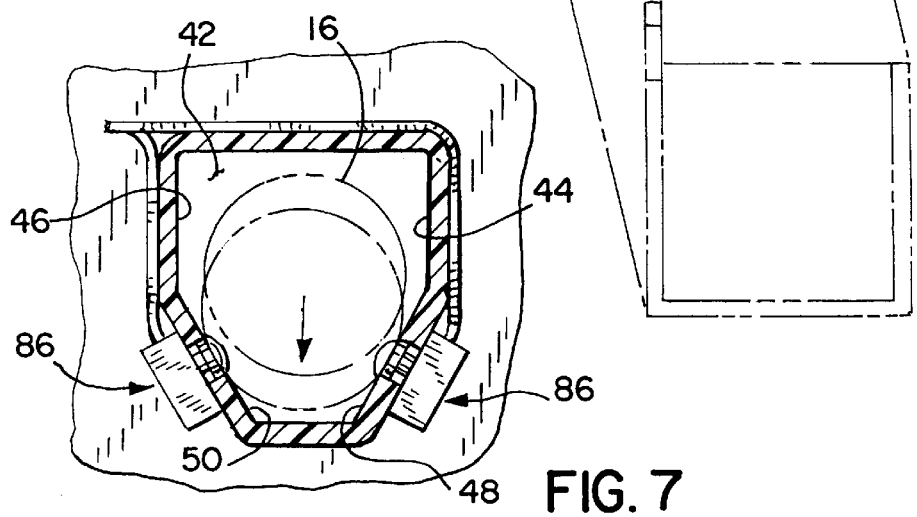

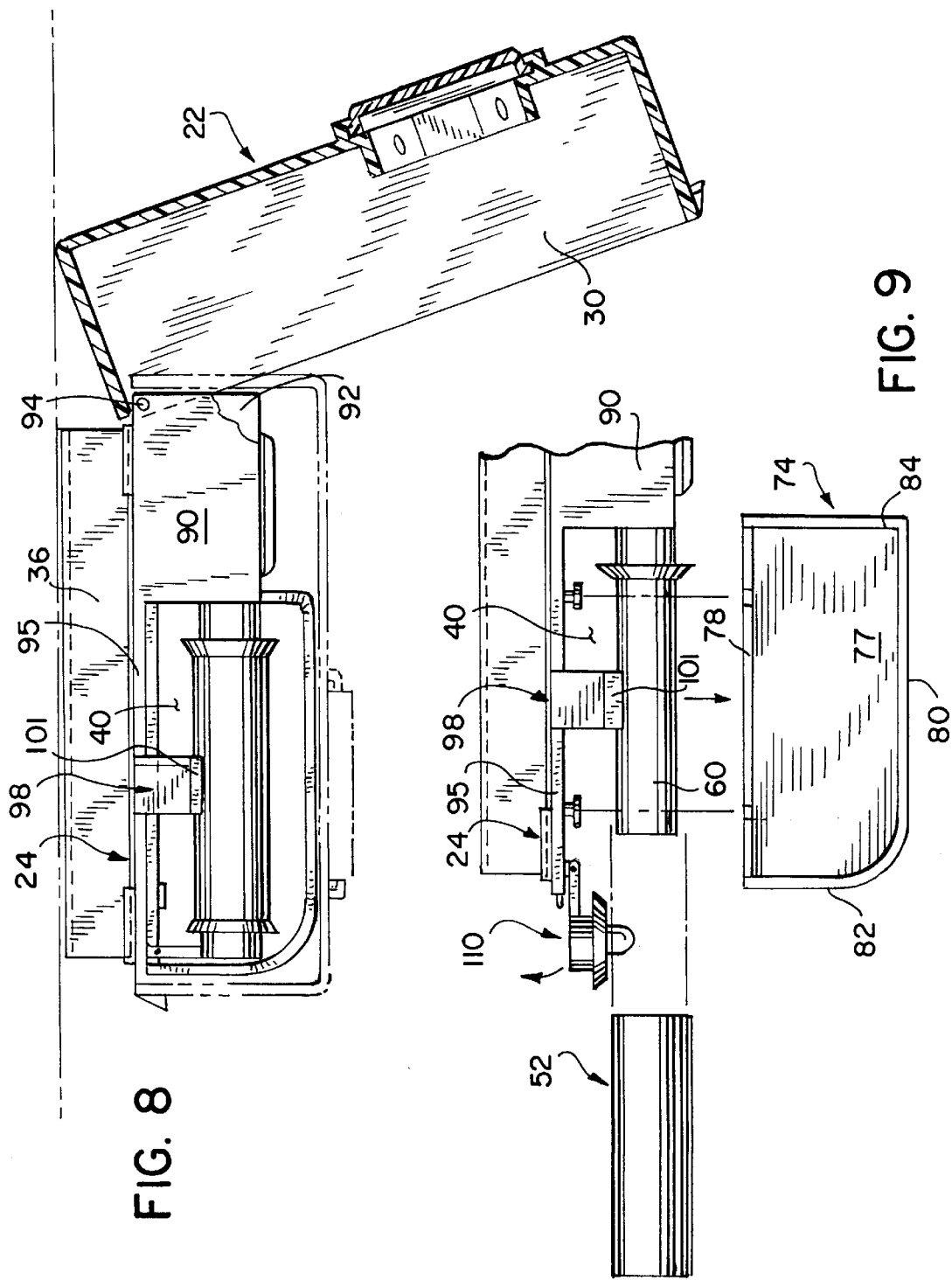

APPARATUS FOR CLEANING A STETHOSCOPE

FIELD OF THE INVENTION

The present invention generally relates to medical instruments and, more particularly, to an apparatus for cleaning a head portion of a medical stethoscope to inhibit transfer of nosocomial infections or other contaminants through use of the stethoscope amongst different patients.

BACKGROUND OF THE INVENTION

Significant advances have been and are continuing to be made in medical technology. Despite such advances, stethoscopes remain an invaluable medical tool or instrument to health care providers such as doctors and nurses. Such health care providers routinely use stethoscopes to facilitate the patients medical care by examining the chest, abdomen, and other areas of the patient. Patients in hospitals often require a greater extent of medical care such as surgery or other invasive procedures which leave open wounds. These areas on the patient tend to secret bodily fluids which may be contaminated with infectious agents, including virus such as human immunodeficiency virus (HIV) thereby resulting in possible infection of the head portion of the stethoscope.

Two types of stethoscopes are commonly used by health care providers. A medical worker can use an inexpensive stethoscope that is typically disposed of after each use such as in intensive care units or wards where patients with VRE (Vancomycin Resistant Enterococcus) or MRSA (Methacillin Resistant Staph. Aureus) infections are located. Such disposable stethoscopes, however, are usually ill fitting to the health care provider, poor quality, and often inadequate for detecting subtle human abnormalities. Accordingly, most physicians and nurses use their own stethoscopes. Although health care providers work with only the best intentions of the patient as their paramount concern, often times a health care provider will use a stethoscope on one patient and, then, reuse the stethoscope without specific preventive cleaning or disinfecting measures being carried out between patients. On occasion, a health care provider will swipe the head portion of the stethoscope with an alcohol swab between patients. Such cursory cleaning procedures, however, are often inadequate to completely destroy infectious contaminations on the diaphragm of a stethoscope and are often infrequently used between patients.

Medical emergencies only serve to exacerbate the problem. Often times, medical care providers simply do not have the time necessary to adequately clean the head portion of the stethoscope between patients. Moreover, during rounds, doctors are required to repeatedly pass from one patient's room to the next and yet have enough time to examine additional patients. The manual effort required to adequately clean the stethoscope may, however, detract from the time available to visit and examine patients. On the other hand, reusing the stethoscope without sufficient cleaning care being provided thereto often results in transfer of nosocomial infection or cross contamination between patients.

Thus, there is a need and a desire for an apparatus for cleaning and disinfecting the head portion of the stethoscope in a manner that does not interfere with the health care provider's ability to timely examine patients without concern over transferring nosocomial infection and contaminants between patients.

SUMMARY OF THE INVENTION

In view of the above, and in accordance with the present invention, a first aspect of the present invention relates to an apparatus for cleaning and disinfecting a head portion of a medical stethoscope. As is conventional, the head portion of the stethoscope includes a diaphragm capable of transducing medical sounds when positioned during use in juxtaposition relative to a patient. The cleaning apparatus of the present invention includes a housing defining an interior cleaning chamber and having an opening communicating between an exterior of the housing and the cleaning chamber. The opening in the housing permits the head portion of the stethoscope to be inserted into the cleaning chamber. An apparatus is arranged in the cleaning chamber for disinfecting the head portion of the stethoscope inserted through the opening.

In a preferred form of the invention, the housing has a multi-walled configuration with the opening extending through one wall portion of the housing to allow the head portion of the stethoscope to be inserted into the cleaning chamber. In a most preferred form of the invention, the housing includes support structure for supporting the head portion of the stethoscope such that the head portion remains in an isolated and inserted relationship within the cleaning chamber without further action being required on the part of a health care provider. Preferably, the housing of the cleaning apparatus is configured to be supported from a stationary support surface thereby allowing the cleaning apparatus to be wall mountable adjacent a doorway of a patient's room.

To permit access to the interior cleaning chamber, when required, the housing of the present invention is preferably configured as a two-piece sealed assembly. That is, according to a preferred form of the invention, the housing includes a base member with a cover arranged in releasable but sealed relationship relative to the base member. The cover includes a front wall portion with multiple wall portions extending rearwardly from the front wall portion. As will be appreciated, the front wall portion preferably defines the opening for allowing the head portion of the stethoscope to be inserted into the cleaning chamber.

The apparatus arranged in the cleaning camber for disinfecting the head portion of the stethoscope can take a myriad of forms. In one form, the disinfecting apparatus includes a cleaning member of resilient material positioned in the cleaning chamber for engagement with the head portion of the stethoscope inserted into the chamber for cleaning. The resilient member can form part of a rotating assembly arranged to engage and clean the head portion of the stethoscope inserted into the cleaning chamber.

The rotating assembly comprising a portion of the disinfecting cleaner preferably includes a pair of elongated rollers or shafts arranged within the housing for rotation about generally parallel and spaced apart axes. A belt is drivingly entrained about the shafts for rotation therewith. As will be appreciated, the belt is impregnated with a suitable cleaning solution to disinfect the head portion of the stethoscope inserted into engagement therewith. In this embodiment of the invention, the housing preferably defines a plate-like member arranged to one side of the belt opposite from the insert opening for supporting a lengthwise section of the belt from deflecting beyond a predetermined limit in response to the head portion of the stethoscope being pressed thereagainst for cleaning purposes.

In an alternative embodiment of the invention, the cleaning apparatus arranged in the cleaning chamber of the housing includes a spray mechanism for directing a fluid spray in a predetermined pattern toward the head portion of the stethoscope inserted and isolated in the leaning chamber. In one form of the invention, the spray can include a suitable cleaning solution directed in mist or atomized form toward the head portion of the stethoscope. In the embodiment discussed above, as well as this second embodiment of the invention, a sump is provided preferably at the bottom of the housing for holding a reservoir of cleaning solution. In another form of the invention, however, the fluid stream directed toward the head portion of the stethoscope can constitute a stream of heated air. The air directed toward the head portion of the stethoscope being heated to a temperature sufficient to destroy contaminants on the head portion of the stethoscope but without adversely altering the stethoscope diaphragm.

In a preferred form of the invention, the disinfecting apparatus operates as a function of the presence of the head portion of the stethoscope being inserted through the insert opening for cleaning purposes. According to a preferred from of the invention, the insert opening is configured with camming surfaces which position and hold the head portion of the stethoscope. A sensor apparatus monitors the insertion of the head portion of the stethoscope into the insert opening and operates a motor used to drive the disinfecting apparatus as a function of signals received from the sensor apparatus. Preferably, the motor drives the disinfecting apparatus at various speeds. In a preferred form of the invention, batteries or another suitable power source is provided to drive the motor used to operate the disinfecting apparatus of the present invention.

To inhibit the interior cleaning chamber from inadvertent infection or contamination, the housing preferably further includes a door for releasably closing the insert opening through which the head portion of the stethoscope is inserted for cleaning purposes. Moreover, in a most preferred form of the invention, a pad is arranged on the exterior surface of the housing. The pad is provided to allow the health care provider to wipe the head portion of the cleaning apparatus after it is removed from the cleaning chamber.

According to another aspect of the present invention, there is provided a method of inhibiting passage of nosocomial infection and contamination between patients during use of a medical stethoscope. The method according to the present invention includes the steps of: providing a stethoscope cleaning apparatus in proximal relation to each patient; with the cleaning apparatus including an apparatus for isolating the diaphragm and head portion of the stethoscope and an apparatus for cleaning and disinfecting the head portion of the stethoscope; placing the head portion of the stethoscope into the cleaning apparatus; and operating the cleaning apparatus to disinfect the head portion thereof prior to subsequent use thereof thereby inhibiting cross infection between patients during use of the same stethoscope.

This aspect of the invention further includes the step of supporting the head portion of the stethoscope as the cleaning apparatus is operated. Moreover, this aspect of the present invention furthermore includes the step of sensing the presence of the head portion of the stethoscope within the cleaning chamber of the cleaning apparatus.

The step of operating the cleaning apparatus preferably involves directing cleaning fluid against the diaphragm and head portion of the stethoscope. In a preferred form, the step of directing cleaning fluid against the diaphragm of the stethoscope involves moving a cleaning element impregnated with cleaning fluid into cleaning relationship relative to the diaphragm of the head portion of the stethoscope. According to one form of the invention, moving a cleaning element into cleaning relationship with the diaphragm portion of the stethoscope involves rotating an impregnated element past the diaphragm of the head portion of the stethoscope.

In operation, the stethoscope cleaning apparatus is disposed to receive a head portion of the stethoscope into the cleaning chamber through the insert opening in the housing. Upon insertion of the head portion through the opening, the disinfecting apparatus is operated to effect cleaning and disinfection of the diaphragm of the stethoscope. In the preferred form of the invention, the health care provider inserts the head portion of the stethoscope through the insert opening and the housing of the cleaning apparatus is configured to support the stethoscope without further involvement of the health care provider. This invention enables the head portion of the stethoscope to be cleaned easily, quickly and reliably, thus, significantly reducing if not eliminating nosocomial infection and contamination between patients subjected to the use of the same stethoscope.

These and other objects, aims and advantages of the present invention will become readily apparent from the following detailed description, drawings, and appended claims.

DESCRIPTION OF THE DRAWINGS

FIG. 5 is an enlarged cross-sectional view taken along line 5—5 of FIG. 3;

FIG. 6 is a cross-sectional view taken along line 6—6 of FIG. 3 and illustrating a head portion of the stethoscope inserted for cleaning within a cleaning chamber;

FIG. 7 is a cross-sectional view taken along line 7—7 of FIG. 5;

FIG. 8 is a top plan view with a cover of the present invention shown in section and moved to a position to show the interior of the cleaning apparatus of the present invention;

FIG. 9 is a fragmentary view similar to FIG. 8 but showing various components of the present invention in disassembled relation relative to each other;

DETAILED DESCRIPTION OF THE PRESENT INVENTION

Figure 1:
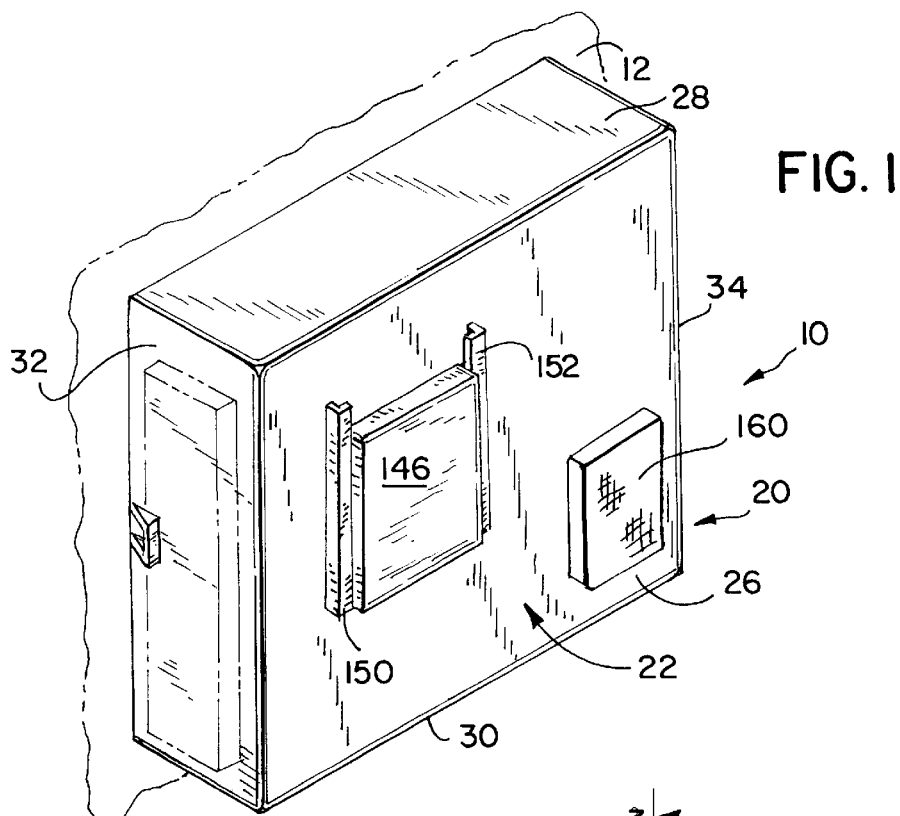
FIG. 1 is a perspective view of the stethoscope cleaning apparatus according to the present invention.

While the present invention is susceptible of embodiment in various forms, there are shown in the drawings and will hereinafter be described preferred embodiments of the invention with the understanding that the present disclosure is to be considered as setting forth exemplifications of the invention which are not intended to limit the invention to the specific embodiments illustrated.

Figure 2:
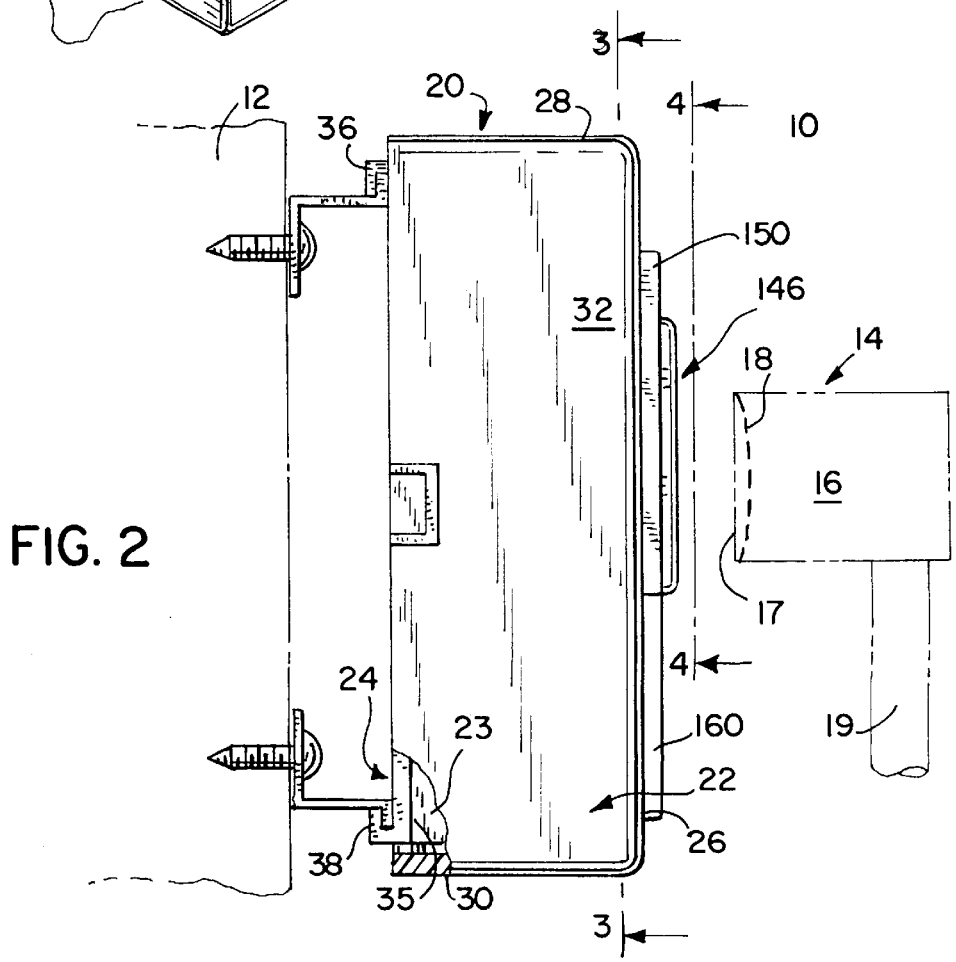
FIG. 2 is an enlarged side elevational view of the cleaning apparatus illustrated attached to a support surface and showing a stethoscope about to be inserted for cleaning into the cleaning apparatus.

Referring now to the drawings, wherein like reference numerals indicate like parts throughout the several views, a stethoscope cleaning apparatus, embodying features of the present invention, is generally indicated in FIGS. 1 and 2 by reference numeral 10. The cleaning apparatus 10 is preferably configured for releasable attachment to a stationary support surface 12 such a wall or the like.

The stethoscope cleaning apparatus 10 of the present invention is adapted to operate in combination with a conventional medical stethoscope, schematically represented in phantom lines in FIG. 2, and generally indicated by reference numeral 14. Suffice it to say, and as is typical of such medical instruments, the stethoscope 14 includes a head portion 16 having a face 17 with a well known diaphragm 18 capable of transducing medical sounds when positioned during use in juxtaposition relative to a patient. Moreover, a conventional stethoscope 14 further includes a medical sound tube portion 19 leading from the head portion 16.

Figure 3:
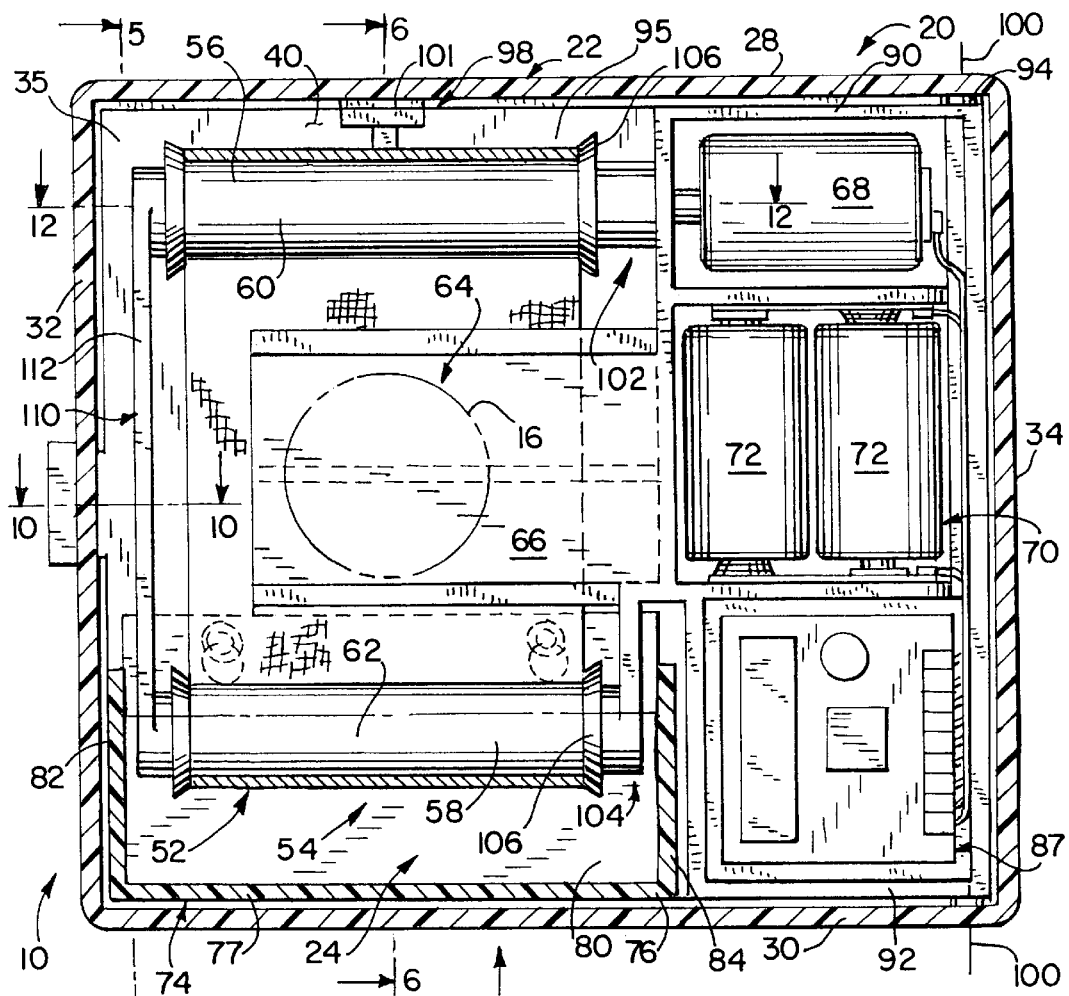
FIG. 3 is an enlarged cross-sectional view taken along line 3—3 of FIG. 2.

As shown, the cleaning apparatus 10 of the present invention includes a housing 20. In the illustrated embodiment of the invention, housing 20 has a multi-walled configuration. In a most preferred form of the invention, and as shown in FIGS. 2 and 3, housing 20 includes a cover 22 mounted in a releasable and sealable association with a base 24. Preferably, cover 22 and base 24 are formed from a plastic or other material that is substantially non-permeable to liquids.

As shown in FIGS. 1, 2 and 3, cover 22 includes a front wall portion 26 with multiple wall portions extending rearwardly therefrom. In the illustrated embodiment of the invention, cover 22 includes top and bottom generally parallel wall portions 28 and 30 rigidly joined to opposite and generally parallel side wall portions 32 and 34; with all the wall portions 28, 30, 32 and 34 being joined to each other and extending rearwardly from the front wall portion 22.

As shown best in FIG. 2, the base 24 of housing 20 is configured with suitable brackets 36 and 38 extending rearwardly therefrom for facilitating releasable attachment of the housing 20 to the stationary support surface 12. As will be appreciated, the brackets 36, 38, for releasably attaching the housing 20 to the support surface 12, may take a form other than that shown without detracting or departing from the spirit and scope of the present invention. For example, apertured hangers or mating lengths of Velcro or the like can be attached to or formed into the housing 20.

Figure 4:
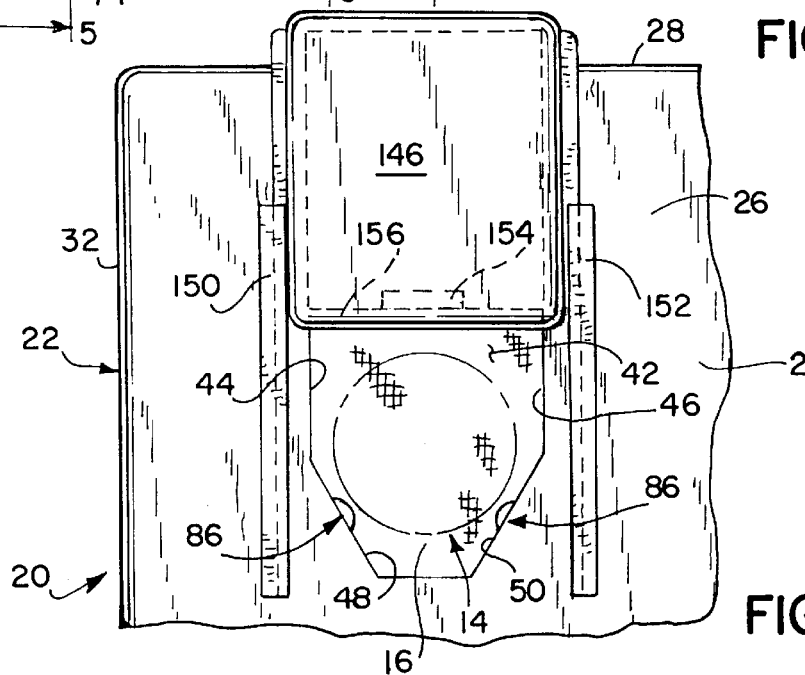
FIG. 4 is an enlarged fragmentary front elevational view taken along line 4—4 of FIG. 2.

As shown in FIG. 5, the housing 20 defines an interior cleaning chamber 40 defined between interior surfaces 23 of cover 22 and the interior surface 35 of the base 24. As shown in FIGS. 4 and 6, an inlet or insert opening 42 is defined in the front wall portion 26 of housing 20. The insert opening 42 extends between the exterior of housing 20 and the cleaning chamber 40 (FIG. 6) for allowing insertion of the head portion 16 of the stethoscope 14 into the cleaning chamber 40.

As shown in FIG. 4, opening 42 is partially defined by a pair of depending and opposed side walls 44 and 46. The side walls 44, 46 are spaced apart by a distance allowing the head portion of any conventional stethoscope to pass therebetween and into the cleaning chamber 40.

In the illustrated embodiment of the invention, the side walls 44, 46 partially defining the opening 42 are specifically configured to positively position and support the head portion 16 of the stethoscope relative to the cleaning chamber 40 without requiring any further support or assistance from a health care provider. That is, after the head portion 16 of the stethoscope is inserted into cleaning chamber 40, gravity causes the head portion 16 of the stethoscope to move toward a lower end of the opening 42. As the head portion 16 of the stethoscope gravitationally moves, the opening 42 is specifically configured to isolate and support the head portion 16 of the stethoscope 14 within the chamber 40.

In the illustrated embodiment of the invention, and as shown in FIGS. 4 and 7, the side walls 44, 46 preferably have a V-shaped configuration extending along at least a portion of their lengths for positively guiding and positioning the head portion 16 of the stethoscope 14 relative to the cleaning chamber 40. As shown in FIG. 4, the side walls 44 and 46 defining opposed sides of opening 42 preferably define camming surfaces 48 and 50 extending along at least a lengthwise portion of sidewalls 44 and 46, respectively, for positively guiding and positioning the head portion 16 of the stethoscope relative to the cleaning chamber 40. Moreover, in the illustrated embodiment of the invention shown in FIGS. 5 and 6, the side walls 44 and 46 extend rearwardly from the front wall portion 26 of housing 20 and into the cleaning chamber 40 for promoting support of the head portion 16 of the stethoscope in the cleaning chamber 40 without requiring support assistance from a health care provider or others.

Turning now to FIG. 5, a disinfecting apparatus 50 is arranged in the cleaning chamber 40 for disinfecting the head portion 16 of the stethoscope inserted through the opening 42 (FIG. 6) into the cleaning chamber 40. In that form of the invention illustrated in FIG. 5, the disinfecting apparatus 50 includes a cleaning member 52 of resilient material such as cloth which tends to absorb and hold liquids and, yet, will not scratch or abrade the face of the diaphragm portion 18 (FIG. 2) of the stethoscope 14 inserted into engagement therewith. The resilient member 52 is positioned in the cleaning chamber 40 for engagement with the face of the head portion 16 of the stethoscope after the head portion 16 of the stethoscope 14 is inserted through the inlet or insert opening 42.

In the embodiment of the invention shown in FIGS. 5 and 6, the resilient member 52 is configured as a belt and forms part of a rotating assembly 54. As illustrated in FIG. 3, the rotating assembly further includes a pair of roller shafts 56 and 58 that are arranged for rotation within the cleaning chamber 40 and about axes 60 and 62, respectively, extending in generally parallel relation relative to each other. As shown, the belt 52 is entrained in driving relation about the roller shafts 56 and 60 and rotates therewith. In the illustrated form of the invention, each roller shaft 56, 58 has a hollow core 59 (FIG. 6) opening to opposite ends thereof As will be appreciated from an understanding of the present invention, the shafts 56 and 58 of the rotating assembly 54 are positioned within the cleaning chamber 40 such that a lengthwise portion of the belt 52 is positioned relative to the opening 42 such that it engages and presses against the head portion of the stethoscope inserted through the opening 42 to thoroughly clean and disinfect the entire stethoscope head portion 16 including the diaphragm 18 from nosocomial infection and contaminants. The belt 52 is impregnated with a suitable cleaning solution to disinfect the head portion 16 of the stethoscope inserted into engagement therewith. The cleaning solution can be of any suitable bacteriocidal solution which operably sterilizes and effectively disinfects a surface contacted thereby and preferably has a relatively low rate of evaporation. A cleaning solution such as chlorhexadine is but one type of disinfectant that readily lends itself to the present invention.

In this embodiment of the invention, and as shown in FIGS. 3 and 6, housing 20 is provided with a support 64 for facilitating cleaning of the head portion 16 of the stethoscope 14 following its insertion into the cleaning chamber 40 of the cleaning apparatus of the present invention. More specifically, the base 24 of housing 20 is configured to provide a plate-like member 66 arranged to one side of the belt 52 opposite from the insert opening 42. The purpose of the plate-like member 66 is to support a lengthwise portion of the belt 52 opposite from the insert opening 42 from deflecting beyond a predetermined limit in response to the head portion 16 of the stethoscope 14 being pressed thereagainst for cleaning purposes.

Returning to FIG. 3, the illustrated form of rotating assembly 54 further includes a motor 68 for rotatably driving at least one of the rollers 56, 58 and, thereby, the belt 52 drivingly entrained thereabout. The motor 68 is connected to a suitable power source 70 which, in the illustrated embodiment, includes batteries 72 but may likewise be any common electrical source.

As shown in FIGS. 3, 5 and 6, housing 20 of the cleaning apparatus 10 of the present invention preferably further includes a sump 74 for holding a supply of suitable cleaning fluid therein. Notably, in the illustrated form of the invention, a lengthwise portion of the belt 52 of the rotating assembly 54 passes through the sump 74 to effect a cleaning action of the belt 52 and to adequately moisten the belt 52 to thoroughly cleanse the head portion 16 of the stethoscope 14 intended to be cleansed thereby. A heater (not shown) can be disposed within the sump 74 for warming the cleaning solution, thus prewarming the head portion 16 of the stethoscope.

As shown in FIGS. 3, 5 and 6, sump 74 preferably includes a liquid tight housing 76 having a bottom wall portion 77 joined to upstanding front and back wall portions 78 and 80, respectively, and to side wall portions 82 and 84. The wall portions 77, 78, 80, 82 and 84 of housing 76 are configured to offer a depth to the housing 76 capable of holding a significant amount of suitable cleaning fluid therein. As shown, the back wall 78 of housing 76 is configured for releasable attachment to the interior surface 35 of base 24. Suffice it to say, the housing 76 of sump 74 is positioned within the interior cleaning chamber 40 of housing 20 such that at least a portion of the belt 52 entrained about roller shaft 58 passes through the cleaning fluid in the sump 74 as the disinfecting apparatus 50 is operated.

In a preferred form of the invention, the rotating assembly 54 is driven at variable speeds. As shown in FIG. 7, at least one sensor 86 is mounted in proximity to the insert opening 42 for monitoring when the stethoscope head portion 16 is presented for cleaning and for controlling operation of the disinfecting apparatus 50 as a function thereof In the illustrated form of the invention, the sensor 86 is provided along the length of at least one of the camming surfaces 48, 50. As will be appreciated, as the head portion 16 of the stethoscope 14 is positioned by the camming surface 48, 50 relative to the interior cleaning chamber 40 and the disinfecting apparatus 50, the sensor 86 detects the presence of the stethoscope head portion 16 and signals the motor 68 to operate the disinfecting apparatus 50.

The sensor 86 may be of any suitable type including photosensor, infrared and etc. Preferably, sensor 86 includes a plunger which, in response to displacement thereof enables circuitry 87 (FIG. 3) carried by housing 20 to control the motor 68 so as to operate the disinfecting apparatus 50 only when the stethoscope head portion 16 is passed through the insert opening 42 for cleaning in the interior chamber of the cleaning apparatus 10. As shown, preferably two sensors 86 and 86' are operated in combination relative to each other for detecting the presence of a stethoscope head portion 16 being presented for cleaning purposes within the cleaning chamber 40 of the cleaning apparatus 10 of the present invention.

To allow service access to the interior cleaning chamber 40, and, thus, to the disinfecting apparatus 50, cover 22 is movably attached to the base 24 of housing 20. As shown in FIGS. 3 and 8, base 24 is provided with generally parallel upper and lower flanges 90 and 92, respectively, projecting forwardly from a back plate 95 forming part of base 24. The vertical dimension separating the upper and lower flanges 90 and 92 is equal to or slightly less than the vertical distance separating the top and bottom wall portions 28 and 30, respectively, of cover 22. A vertically elongated pin 94 passes through the top and bottom wall portions 28 and 30, respectively, of the cover 22 as well as through the upper and lower flanges 90 and 92, respectively, of base 24 thereby allowing the cover to pivotally move about a generally vertical axis 100 (FIG. 3).

As shown in FIG. 8, the cover 22 is movable between a closed or operational position, shown in FIG. 8 in dash lines, and an open or non-operational position, shown in solid lines. As will be appreciated, when the cover 22 is in a closed position, the housing 20 is sealed to inhibit liquids from escaping therefrom. To enhance the sealing ability of the cover 22 relative to base 24, housing 20 may further include suitable seals arranged about the periphery. Such seals, however, have been eliminated from the drawings for purposes of simplicity.

As shown in FIG. 8, once the cover 22 of housing 20 is moved to an open position, access to the interior cleaning chamber 40 is readily achievable. Moreover, opening the cover 22 permits ready access to and, if desired, removal of the sump 74.

Figure 10:
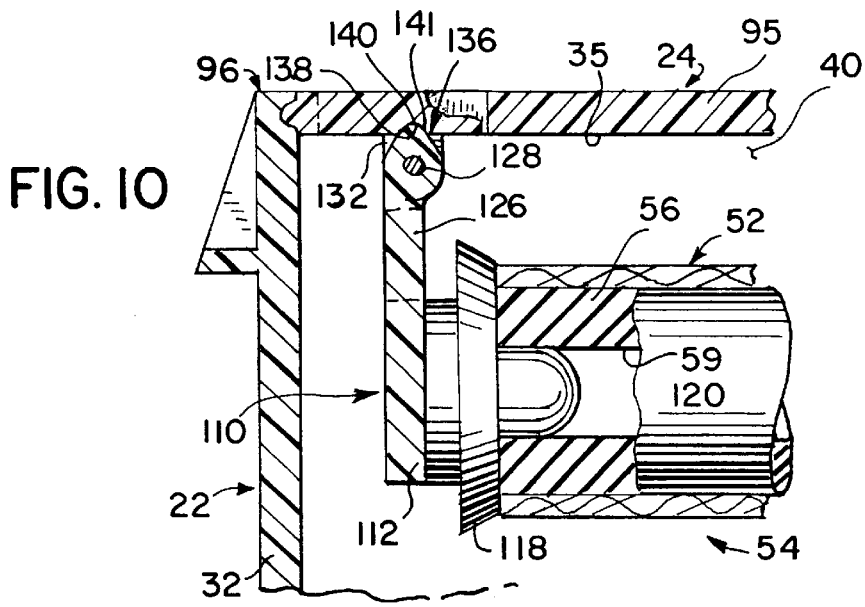
FIG. 10 is an enlarged cross-sectional view taken along line 10—10 of FIG. 3.

As shown in FIG. 10, a suitable latch 96 releasably holds the cover 22 in locked relationship relative to base 24. Moreover, and as shown in FIGS. 3, 5, 6 and 9, base 24 is provided with a guide 98 to properly position the cover 22 relative to the base 24 when cover 22 is being closed. Preferably, guide 98 has a chamfered lead surface 101. Surface 101 on guide 98 acts as a camming surface to facilitate proper placement of the cover 22 relative to the base 24.

Figure 12:
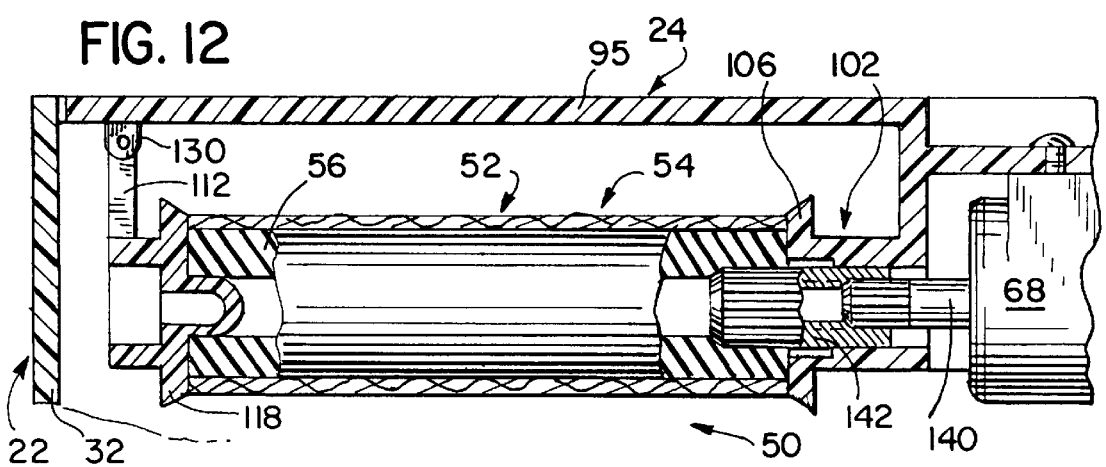
FIG. 12 is a sectional view taken along line 12—12 of FIG. 3.

Opening the cover 22 of housing 20 furthermore permits repair or replacement of the resilient cleaning member 52 or parts of the rotating assembly 54. As shown in FIGS. 3, 6 and 12, base 24 of housing 20 includes a pair of vertically spaced roller supports 102 and 104. Each roller support 102, 104 has a radially enlarged flange 106 toward a distal end thereof for limiting transverse movement of the belt 52 on the roller shaft 56, 58 as the rotating assembly 54 is operated. The roller supports 102, 104 provide rotational support for one end of each roller shaft 56, 58 of the rotating assembly 54.

Opposite ends of the roller shafts 56, 58 are rotatably supported by a displacable support bracket assembly 110. As shown in FIGS. 3, 5 10 and 11, support bracket assembly 110 includes a vertically rigid member 112 having two vertically spaced head portions 114 and 116 arranged toward opposite ends thereof As will be appreciated, the vertical spacing between the head portions 114 and 116 is equal to the vertical spacing between roller supports 102 and 104. Each head portion 114, 116 extends away from the rigid member 112 and, toward a free end thereof includes a radially enlarged flange 118 similar to flange 106 toward a free end thereof. Notably, the transverse distance separating the flanges 118 of head portions 114, 116 from the flanges 106 of roller supports 102, 104 is substantially equal to the length of the roller shafts 56, 58 and the width of belt 52. As will be appreciated, the flanges 118 of the head portions 114, 116 are suitably configured to limit transverse movement of the belt 52 upon operation of the disinfecting apparatus 50.

Each head portion 114, 116 of bracket assembly 110 furthermore includes a pilot 120 extending therefrom. The pilot 120 is sized to snugly fit within the internal bore or core 59 of a respective roller shaft 56, 58 supported thereby. As shown, the free end of each pilot 120 preferably has a semi-spherical configuration to facilitate insertion of the pilot 120 into the respective bore or opening 59 of a respective roller support 56, 58 of the rotating assembly 54.

Figure 11:
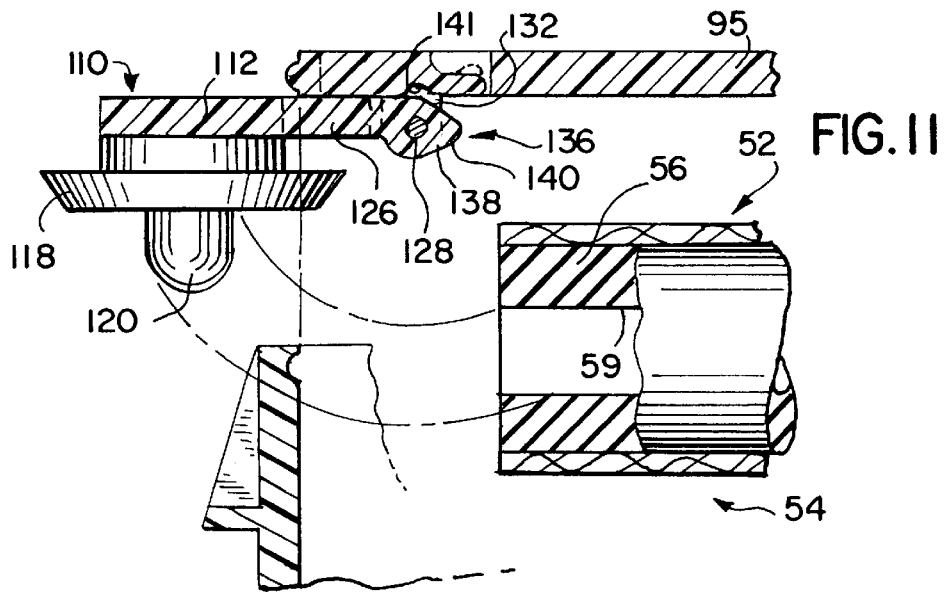
FIG. 11 is a sectional view similar to FIG. 10 but showing components of the present invention in disassembled relation relative to each other.

The support bracket assembly 110 is mounted to readily allow for repair or replacement of component pieces of the roller assembly 54. In the illustrated form of the invention, and as shown in FIG. 9, the support bracket assembly 110 is mounted to allow for pivotal movement thereof about a generally vertical axis 124 (FIG. 5) thus allowing for disassembly and repair of the components of the disinfectant apparatus 50. As shown in FIGS. 5, 10 and 11, the rigid member 112 is preferably provided with a rigid mounting arm 126 that extends rearwardly from the rigid member 112 and is pivotally joined, as by a pin 128, defining the pivot axis 124 of the bracket assembly 110, to a pair of ears 130 (FIG. 12) and 132 (FIGS. 10 and 11) projecting forwardly from the back plate 95 of base 24 of housing 20.

A locking apparatus 136 releasably maintains the bracket assembly 110 in an operable position, shown in solid lines in FIG. 10, and permits the bracket assembly 110 to be readily and easily released to a non-operative position, as shown in FIG. 11. In the preferred form of the invention, the locking apparatus 136 includes a generally pointed projection 138 formed on the rearend of the rigid arm 126 of member 112 of bracket assembly 110. As shown in FIGS. 10 and 11, the projection 138 is configured such that a free tip portion 140 of the projection 138 is axially aligned with the arm 126 of rigid member 112 and the pivot pin 128 but projects rearwardly away from the pin 128 a greater distance than does the remaining portion of projection 138.

A suitably shaped slot or channel 141 is defined by the base 24 of housing 20 for releasably accommodating the projection 138 of the rigid arm 126. As shown in FIGS. 10 and 11, and in the area of the channel 141, base 24 of housing 20 has a reduced cross-sectional configuration and is preferably configured as a leaf spring with the channel 141 being disposed toward a distal end of the spring.

The proposed leaf spring design allows the spring to resiliently flex or deflect (as shown in dotted lines in FIG. 11) when the projection 138 on arm 126 is required to move therepast, and then resiliently return to its normal condition thereby releasably holding the bracket assembly 110 in place. In the illustrated embodiment of the invention, the locking apparatus 136 is configured such that the bracket assembly 110 is normally retained in generally perpendicular relationship relative to the base 24 of housing 20. As should be appreciated, suitable seals (not shown) would preferably be arranged about the leaf spring of the base 24 to inhibit cleaning fluid from leaking or splashing out from the interior cleaning chamber 40 during operation of the cleaning apparatus 10 of the present invention.

In the preferred form of the invention, and as shown in FIG. 12, the rotating assembly 54 is preferably directly driven from the motor 68. As shown, motor 68 includes a rotatable output drive shaft 140 with an axially splined configuration at the distal end thereof. Preferably, roller shaft 56 includes a generally hollow stub shaft 142. As shown, a lengthwise portion of shaft 142 telescopically extends within the bore 59 of roller shaft 56 and another lengthwise portion extends axially outward from the bore 59 defined by roller shaft 56. That portion of the stub shaft 142 axially extending from the bore 59 of shaft 56 is journalled for free rotation within the roller support 102 of base 24.

To promote and maintain a positive driving relationship between the roller shaft 56 and shaft 142, that portion of shaft 142 telescopically extending within the bore 59 of roller shaft 54 is preferably axially splined. The remaining outer diameter of shaft 142 preferably has a smooth outer configuration to promote free turning movement within the support 102 of base 24. When assembled, the splined output shaft 140 of motor 68 is pressed within the hollow interior of shaft 142 thereby effecting a positive rotational drive connection of the motor 68 to roller shaft 56.

To inhibit contaminants from inadvertently passing into the interior cleaning chamber 40 through insert opening 42, housing 20 preferably includes a manually displacable door 146 for removably closing the insert opening 42. As shown in FIGS. 1 and 4, door 146 is preferably arranged for generally vertical displacement along a predetermined path of travel and relative to insert opening 42. In the preferred form of the invention, the predetermined path of travel of door 146 is defined by a pair of tracks 150 and 152 relative to which the door 146 is slidably mounted and which maintain the door 146 in substantially sealed proximity to the front wall portion 26 of housing 20 when the door is in a closed position.

As shown in FIGS. 4 and 6, an outwardly projecting lip or stop member 154 on housing 20 cooperates with a jam 156 on the door 146 to limit vertical displacement of the door 146 relative to the insert opening 42. Suffice it to say, when door 146 is in an open position (FIG. 4), more than sufficient room or space is provided allow a health care provider to insert the head portion 16 of the stethoscope 14 into the insert opening 42 of the cleaning apparatus of the present invention. Preferably, the door 146 will automatically close (FIG. 1) when nothing lies in the predetermined path of movement of the door 146.

When the cleansed stethoscope head portion 16 is removed from the cleaning chamber 40, some residual cleaning solution may remain on the diaphragm portion 18 of the stethoscope 14. In a preferred form of the invention, a pad 160 may be releasably attached as with Velcro or the like to the exterior of the housing 20. As will be appreciated, the releasable configuration facilitates replacement of the pad 160 to the housing 20. The pad 160 is formed from a suitable liquid absorbent substance that will not damage the diaphragm portion 18 of the stethoscope when the latter is swiped therepast. By such construction, the health care provider merely needs to swipe the head portion 16 of the cleansed head portion 16 of the stethoscope 14 into contact with the pad 160 to remove any residual cleaning solution that may remain thereon after the stethoscope head portion 16 is removed from the cleaning chamber 40.

Another embodiment of a cleaning apparatus according to the present invention is schematically represented in FIG.

Figure 13:
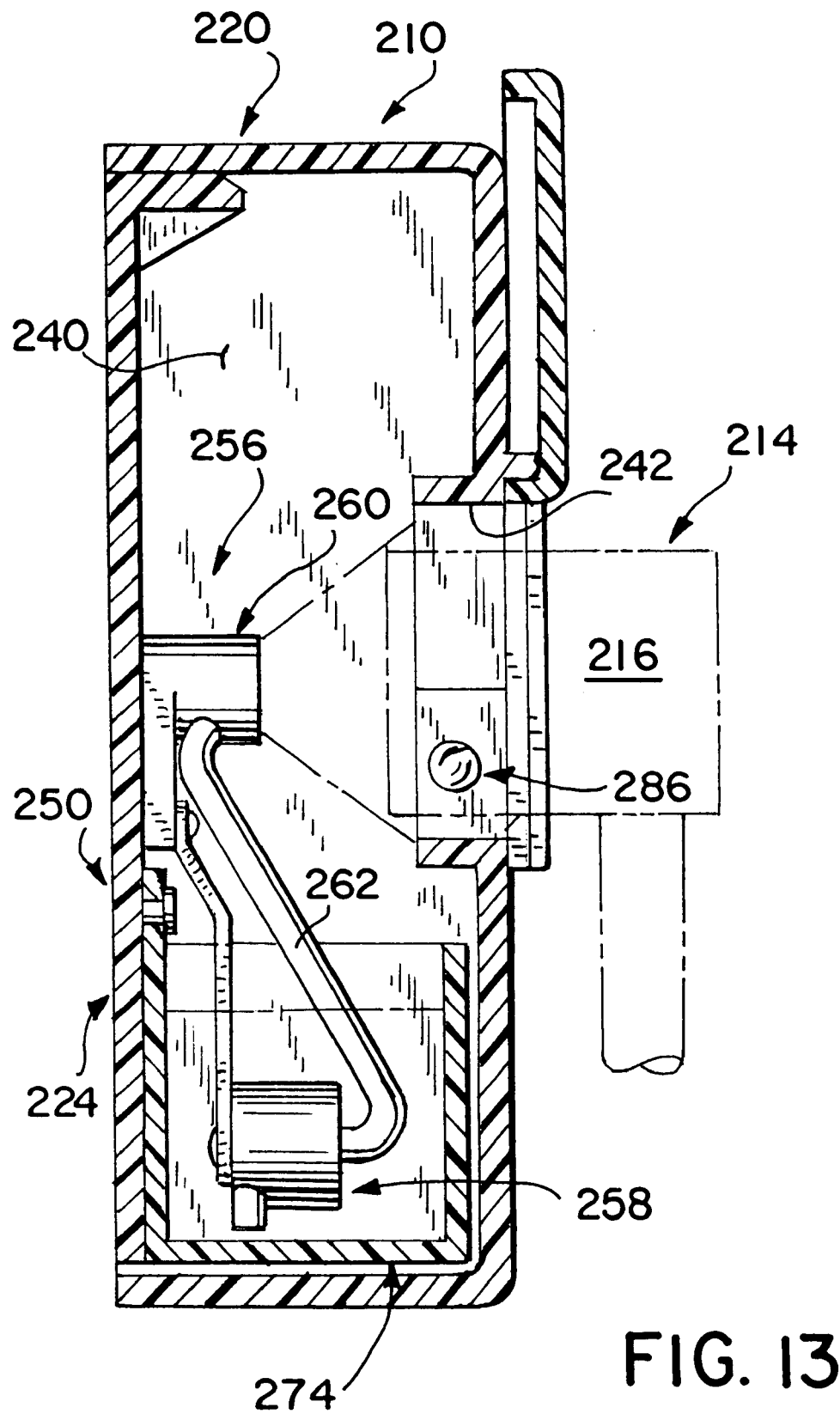
FIG. 13 is an alternative embodiment of the present invention.

13. This alternative form of cleaning apparatus shown in FIG. 13 is designated generally by reference numeral 210. The elements of this alterative form of cleaning apparatus that are identical to or functionally analogous to those components mentioned above with respect to cleaning apparatus 10 are designated by the same reference numerals identical to those above with the exception that this embodiment uses reference numerals in the 200 series.

In this embodiment of the invention, the housing 220 is substantially similar to that discussed above except the base 224 of the housing 220 does not require the spring like formation for releasably locking portions of the disinfecting apparatus in place. Suffice it to say, this embodiment of the cleaning apparatus 210 likewise includes a sump 274 for holding a supply or reservoir of cleaning solution within the interior cleaning chamber 240 of housing 220. A head portion 216 of a stethoscope 214 is insertable into the interior cleaning chamber 240 through an insert opening 242 provided on housing 220.

A disinfecting apparatus 250 is arranged in the interior cleaning chamber 240 of the cleaning apparatus 210. In this embodiment of the invention, the disinfecting apparatus 250 includes a spray mechanism 256. The spray mechanism 256 includes a motor driven pump assembly 258 operably arranged in the sump 274 and a nozzle-like spray apparatus 260 mounted in the interior chamber 240 for directing a spray mist of cleaning solution in a predetermined pattern toward the head portion 216 of the stethoscope inserted into the chamber 240 for cleaning. A suitable conduit or passage 262 interconnects the pump assembly 258 to the nozzle-like spray apparatus 260.

Like the embodiment of the invention discussed above, the spray mechanism 256 of the cleaning apparatus 210 is operated as a function of the position of the of the head portion 216 of the stethoscope 214 relative to the insert opening 242. To accomplish such ends, this embodiment of the invention includes one or more suitable sensors 286 arranged adjacent the inlet opening 242 for monitoring when the head portion 216 of the stethoscope 214 is inserted for cleaning into the cleaning chamber 240 of the cleaning apparatus 210. As will be appreciated from an understanding of the invention, when the sensor 286 detect the head portion 216 of the stethoscope is inserted for cleaning into the cleaning chamber 240, the spray mechanism 256 is timely operated. Moreover, operation of the spray mechanism 256 will be automatically discontinued after the stethoscope head portion 216 is removed from the inlet opening 242.

Figure 14:
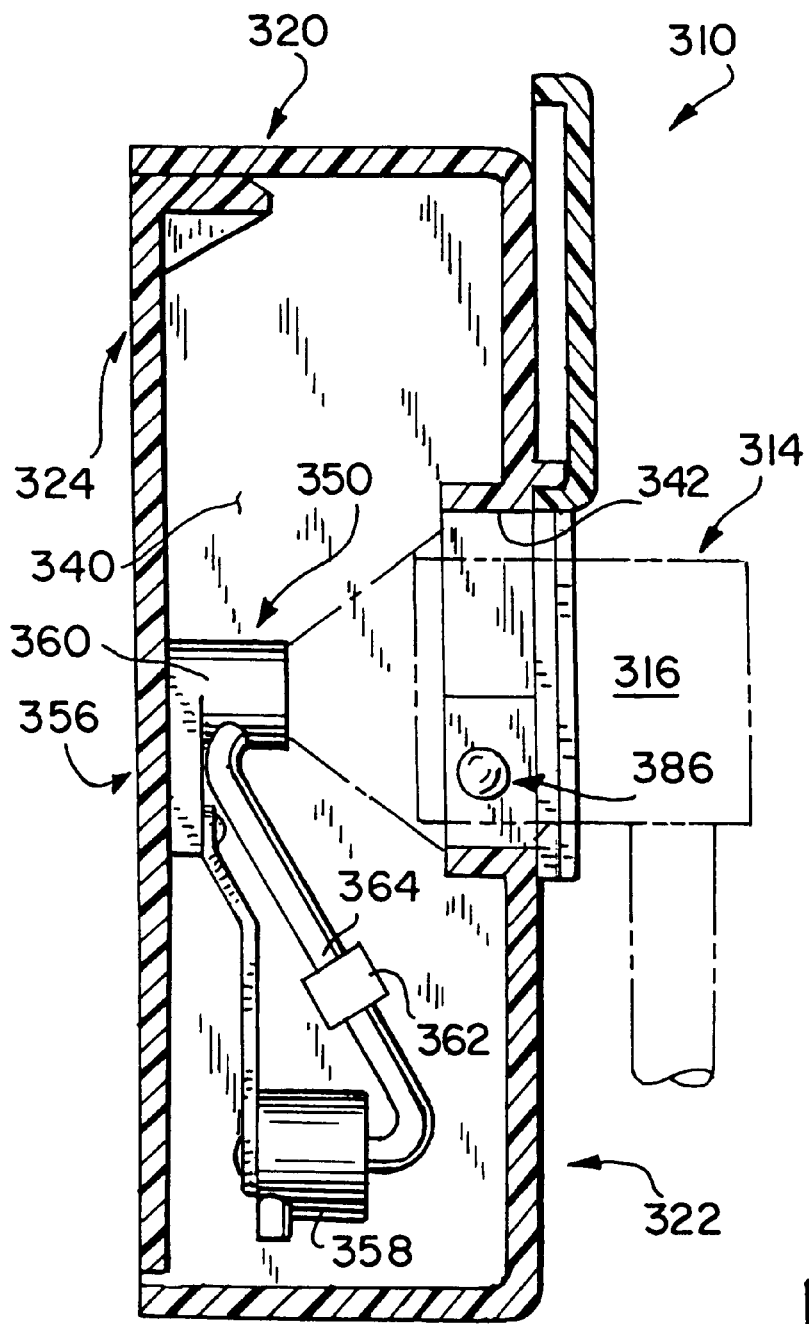
FIG. 14 is another alternative embodiment of the present invention.

Another embodiment of cleaning apparatus according to the present invention is schematically represented in FIG. 14. This alternative form of cleaning apparatus shown in FIG. 14 is designated generally by reference numeral 310. The elements of this alterative form of cleaning apparatus that are identical to or functionally analogous to those components mentioned above with respect to cleaning apparatus 10 are designated by the same reference numerals identical to those above with the exception that this embodiment uses reference numerals in the 300 series.

In this embodiment of the invention, the housing 320 is substantially similar to that discussed above with respect to housing 20 except the base 324 of the housing does not require the spring like formation for releasably locking portions of the disinfecting apparatus in place. Moreover, with this embodiment of the invention, the cover 322 of housing 320 does not require a sealing engagement with the base 324 in the manner described with the embodiments disclosed above. Suffice it to say, a head portion 316 of a stethoscope 314 is insertable into the interior cleaning chamber 340 through an insert opening 342 provided on housing 320.

A disinfecting apparatus 350 is arranged in the interior cleaning chamber 340 of the cleaning apparatus 310. In this embodiment of the invention, the disinfecting apparatus 350 includes a spray mechanism 356. The spray mechanism 356 includes a motor driven pump assembly 358 arranged in the interior of housing 320, a nozzle-like spray apparatus 360 mounted in the interior chamber 340, and a heater, generally indicated by reference numeral 362. The heater 362 is preferably interposed between the pump assembly 358 and the spray apparatus 360.

The purpose of the spray mechanism 356 is to direct a heated air spray in a predetermined pattern toward the head portion 316 of the stethoscope 314 with sufficient pressure to effect cleaning and disinfection of the diaphragm 318 of the stethoscope head portion 316. It should be appreciated that the temperature of the heated air spray directed toward the diaphragm 318 of the stethoscope head portion 316 inserted for cleaning into chamber 340 is controlled such that it is sufficient to disinfect the head portion of the stethoscope but no damage will be caused to the stethoscope's diaphragm 318. A suitable conduit or passage 364 interconnects the pump assembly 358 with the nozzle-like spray apparatus 360.

Like the embodiment of the invention discussed above, the spray mechanism 356 of the cleaning apparatus 310 is operated as a function of the position of the head portion 316 of the stethoscope 314 relative to the opening 342. To accomplish such ends, this embodiment of the invention includes one or more suitable sensors 386 arranged adjacent the insert opening 342 for monitoring when the head portion 316 of the stethoscope 314 is inserted for cleaning into the cleaning chamber 340 of the cleaning apparatus 310.

Another aspect of the present invention relates to a method for inhibiting passage of nosocomial infection and contamination between patients caused through common usage of the stethoscope 14 between different patients. The methodology according to the present invention involves the steps of: providing a stethoscope cleaning apparatus in proximal relation to each patient; with the cleaning apparatus including an apparatus for isolating the diaphragm and head portion of the stethoscope and an apparatus for cleaning and disinfecting the head portion of the stethoscope; placing the head portion of the stethoscope into the cleaning apparatus; and, operating the cleaning apparatus to disinfect the head portion thereof prior to subsequent use thereof thereby inhibiting cross infection between patients during use of the same stethoscope.

This aspect of the invention is enhanced by including the further step of supporting the head portion of the stethoscope as the cleaning apparatus is operated. Further advantages have been realized with this aspect of the present invention by including the step of sensing the presence of the head portion of the stethoscope within the cleaning chamber of the cleaning apparatus.

The step of operating the cleaning apparatus preferably involves directing a stream of cleaning fluid (whether it is a liquid cleaning and disinfecting solution or heated air) against the diaphragm and head portion of the stethoscope. According to a preferred methodology, the step of operating the cleaning apparatus involves moving a cleaning element impregnated with cleaning fluid past the diaphragm of the head portion of the stethoscope. As discussed above, the step of moving a cleaning element past the diaphragm can involve rotating an impregnated element past the diaphragm of the head portion of the stethoscope.

Although an understanding of the present invention is readily achieved from the foregoing description, a brief summary of the operation of the present invention will be provided to merely supplement that which was disclosed above. For purposes of succinctness, operation of only the first embodiment of the invention will be summarized with the understanding the other embodiments are self-explanatory thereafter. The stethoscope cleaning apparatus 10 is disposed to receive a head portion 16 of the stethoscope 14 into the cleaning chamber 40 through the insert opening 42 in the housing 20. Upon insertion of the head portion 16 through the opening 42, the disinfecting apparatus 50 is automatically operated to effect cleaning of the diaphragm 18 of the stethoscope 14.

In the preferred form of the invention, the health care provider simply inserts the head portion 16 of the stethoscope 14 through the insert opening 42 with the housing 20 of the cleaning apparatus 10 being configured to support the stethoscope 14 without further involvement of the health care provider. This invention enables the head portion 16 of the stethoscope 14 to be cleaned easily, quickly and reliably, thus, significantly reducing if not elimination nosocomial infection and contamination between patients subjected to the use of the same stethoscope.

Following removal of the head portion 16 of the stethoscope 14 from the cleaning chamber, the health care provider can merely swipe the diaphragm 18 across the pad 160 to dry same before using the stethoscope on a patient. Moreover, after the cleansed head portion 16 of the stethoscope has been removed from the cleaning chamber of the present invention, such removal is sensed by the sensor 86 to effect operation of the disinfecting apparatus 50. Once the head portion 16 of the stethoscope 14 has been removed from the cleaning chamber 40, the door 140 automatically returns to a closed position thereby inhibiting inadvertent contamination of the cleaning chamber 40.

From the foregoing, it will be observed that numerous modifications and variations can be effected without departing from the true spirit and scope of the novel concept of the present invention. It will be appreciated the present disclosure is intended to set forth exemplifications of the invention, and are not intended to limit the invention to the specific embodiments illustrated. The disclosure is intended to cover by the appended claims all such modifications as fall within the scope of the claims.

What is claimed is:

1. A stethoscope cleaning apparatus, comprising:
   a housing defining an interior cleaning chamber and having an opening communicating between an exterior of said housing and said chamber, said opening defining a plane and being configured to permit insertion of a head portion of a stethoscope into said cleaning chamber; and
   a driven bacterial disinfecting apparatus arranged in said cleaning chamber in predetermined relation relative to said opening such that when the head portion of the stethoscope is inserted through the opening and into said cleaning chamber said disinfecting apparatus engages with a face thereof and thereby disinfects the head portion of the stethoscope inserted into said opening, and wherein said bacterial disinfecting apparatus defines a substantially flat cleaning surface facing said opening extending generally parallel to said plane at least over that portion engaging with the face of the stethoscope.

2. The stethoscope cleaning apparatus according to claim 1 wherein the housing is configured to be supported from a stationary support surface.

3. The stethoscope cleaning apparatus according to claim 1 wherein said disinfecting apparatus arranged in said cleaning chamber includes a cleaning member of resilient material absorbent to liquids and positioned in the cleaning chamber for non-abrasive engagement with said head portion of said stethoscope after said head portion is inserted through said opening.

4. The stethoscope cleaning apparatus according to claim 1 wherein the opening defined by said housing is configured to support the head portion of the stethoscope inserted through said opening.

5. The stethoscope cleaning apparatus according to claim 1 further including a sump for holding a supply of bacterial disinfecting fluid therein, said sump being removably carried within said housing to facilitate replacement of the supply of bacterial cleaning fluid held therewithin.

6. The stethoscope cleaning apparatus according to claim 1 wherein said bacterial disinfecting apparatus comprises a pair of rotatable shafts arranged in generally parallel relation relative to each other with a non-abrasive belt entrained about said shafts for rotation therewith, with at least one of said shafts being rotatably driven under power, and wherein said housing further includes movable structure for supporting common ends of said shafts for rotation.

7. The stethoscope cleaning apparatus according to claim 6 wherein said belt is impregnated with a suitable cleaning solution to disinfect the head portion of the stethoscope inserted into engagement therewith.

8. The stethoscope cleaning apparatus according to claim 6 wherein said bacterial disinfecting apparatus further includes a motor carried by said housing for positively driving at least one of said shafts at variable speeds.

9. The stethoscope cleaning apparatus according to claim 1 further including a door arranged on said housing for allowing access to said cleaning chamber.

10. The stethoscope cleaning apparatus according to claim 1 further including a pad arranged on an exterior surface of said housing and against which said head portion of the stethoscope is wiped after being cleaned by said cleaning apparatus.

11. The stethoscope cleaning apparatus according to claim 1 further including a door movable between a closed position, whereat said door closes the opening defined by said housing, and an open position, whereat said door is moved relative to said opening defined by said housing to permit the head portion of the stethoscope to be inserted into said cleaning chamber.

12. A stethoscope cleaning apparatus, comprising:
   a multi-walled housing defining an interior cleaning chamber and an insertion opening defining a plane extending through one wall of said housing and communicating with said chamber for allowing a head portion of a stethoscope to be inserted into said cleaning chamber, said housing further including support structure for supporting the head portion of said stethoscope inserted into said cleaning chamber, and
   a rotatably driven bacterial disinfecting apparatus arranged in said cleaning chamber for positively applying a disinfecting fluid to a face thereof and thereby disinfecting the head portion of the stethoscope inserted through said insertion opening into said chamber, wherein said bacterial disinfecting apparatus defines a substantially flat cleaning surface facing said opening extending generally parallel to said plane at least over that portion engaging the face of the stethoscope.

13. The stethoscope cleaning apparatus according to claim 12 wherein said housing includes a base and a cover arranged in releasably locked association relative to each other.

14. The stethoscope cleaning apparatus according to claim 13 wherein said cover comprises flat interconnected walls including a front wall portion with said insertion opening defined therein, two opposite side wall portions, a horizontal top wall portion and a horizontal bottom wall portion, said side wall portions along with said top wall and bottom wall portions extending rearwardly from said front wall portion.

15. The stethoscope cleaning apparatus according to claim 12 wherein said housing is configured to be supported from a stationary surface.

16. The stethoscope cleaning apparatus according to claim 12 wherein said bacterial disinfecting apparatus arranged in said cleaning chamber includes a non-abrasive cleaning member of resilient liquid permeable material arranged for non-abrasive engagement with said head portion of said stethoscope after said head portion is inserted through said insertion opening.

17. The stethoscope cleaning apparatus according to claim 12 further including a sump for holding a supply of bacterial disinfecting fluid therein for disinfecting the head portion of the stethoscope inserted into said cleaning apparatus, said sump being removably carried within said housing to facilitate replacement of the supply of bacterial disinfecting fluid held therewithin.

18. The stethoscope cleaning apparatus according to claim 12 wherein said bacterial disinfecting apparatus comprises a pair of rotatable shafts arranged in generally parallel relation relative to each other with a non-abrasive belt entrained about said shafts for rotation therewith, with at least one of said shafts being rotatably driven under power, and wherein said housing further includes movable structure for supporting common ends of said shafts for rotation.

19. The stethoscope cleaning apparatus according to claim 18 wherein said belt is impregnated with a suitable bacterial disinfecting solution to disinfect the head portion of the stethoscope inserted into engagement therewith.

20. The stethoscope cleaning apparatus according to claim 18 wherein said housing further comprises a plate-like member arranged to one side of said belt opposite from said insert opening for supporting a lengthwise portion of said belt from deflecting beyond a predetermined limit in response to the head portion of the stethoscope being pressed thereagainst for bacterial disinfecting purposes.

21. The stethoscope cleaning apparatus according to claim 18 wherein said bacterial disinfecting apparatus further includes a motor carried by said housing for positively driving at least one of said shafts at variable speeds.

22. The stethoscope cleaning apparatus according to claim 21 further including a power source carried within the interior of said housing for operating said motor of said bacterial disinfecting apparatus.

23. The stethoscope cleaning apparatus according to claim 18 further including an apparatus for sensing the presence of the head portion of said stethoscope being arranged for disinfection relative to said insertion opening, and wherein said bacterial disinfecting apparatus further includes a motor for driving the belt entrained about said shafts as a function of signals received from said sensing apparatus.

24. The stethoscope cleaning apparatus according to claim 12 further including a door slidably mounted on said housing to releasably close said insertion opening and thereby limiting access to said cleaning chamber.

25. The stethoscope cleaning apparatus according to claim 12 further including a pad arranged on an exterior surface of said housing and against which said head portion of the stethoscope is wiped after being disinfected by said bacterial disinfecting apparatus.

26. The stethoscope cleaning apparatus according to claim 12 further including a door carried by said housing and movable between a closed position, whereat said door closes the insertion opening defined by said housing, and an open position, whereat said door is moved relative to said insertion opening defined by said housing to permit the head portion of the stethoscope to be inserted into said cleaning chamber.

* * * * *